United States Patent [19]
Bringhen et al.

[11] Patent Number: 6,069,170
[45] Date of Patent: May 30, 2000

[54] LIGHT SCREENING COMPOUNDS AND COMPOSITIONS

[75] Inventors: Alain Bringhen, Croix-de-Rozon; Hans Ulrich Gonzenbach; Magali Pochon, both of Geneva, all of Switzerland; Dominique Sidrac, Saint-Julien, France

[73] Assignee: Roche Vitamins Inc., Parsippany, N.J.

[21] Appl. No.: 09/122,117

[22] Filed: Jul. 24, 1998

[30] Foreign Application Priority Data

Aug. 5, 1997 [EP] European Pat. Off. .............. 97113446

[51] Int. Cl.$^7$ .......................... A01N 37/10; A01N 37/12; C07C 229/44

[52] U.S. Cl. .............................. 514/533; 514/538; 560/44

[58] Field of Search ............... 560/44; 514/533, 514/538

[56] References Cited

U.S. PATENT DOCUMENTS

| | | |
|---|---|---|
| 3,079,366 | 2/1963 | Boyle et al. . |
| 3,515,745 | 6/1970 | Tull et al. ................. 260/471 |
| 4,387,089 | 6/1983 | De Polo ..................... 424/59 |
| 5,403,944 | 4/1995 | Frater et al. . |
| 5,443,820 | 8/1995 | Holderbaum et al. . |
| 5,639,446 | 6/1997 | Raspanti et al. . |
| 5,821,380 | 10/1998 | Holderbaum et al. . |

FOREIGN PATENT DOCUMENTS

| | | |
|---|---|---|
| 0 174 832 | 9/1985 | European Pat. Off. . |
| 1 237 059 | 6/1971 | United Kingdom . |

OTHER PUBLICATIONS

Kohji Ozeki, Yasuhiro Ishizuka, Masahiro Sawada, Teru Ichikawa, Makoto Sato and Hideya Yaginuma; Studies on Antiallergy Agent. 1. Synthesis of 1,4–Dihydro–4–oxo–3–quinolinecarboxylic Acids; Sep. 4, 1986; Yakugaku Zasshi, 107, 123–134.

Database CAPLUS on STN, Acc. No. 1987:617458, Ozeki et al., 'Studies on antiallergy agents. 1. Synthesis of 1,4–dihydro–4–oxo–3–quinoliencarboxylic acids.' Yakugaku Zasshi (1987), 107 (2), p123–34.

Database CAPLUS of STN, Acc. No. 1986:515043, Al–Shaar et al.,'Ethene derivatives.' EP174832 A2 (abstract), 1986.

*Primary Examiner*—Gary Geist
*Assistant Examiner*—Brian J. Davis
*Attorney, Agent, or Firm*—Mark E. Waddell; Stephen M. Haracz; Bryan Cave LLP

[57] ABSTRACT

The invention relates to a cosmetic light-screening composition for protecting human skin or human hair against ultraviolett radiation containing at least one compound of formula I

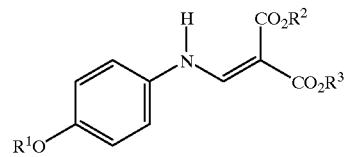

I wherein
$R^1$ represents a $C_{1-8}$ straight or branched alkyl chain, and
$R^2$ and $R^3$ each independently represent a $C_{1-8}$ straight or branched alkyl chain.

27 Claims, No Drawings

LIGHT SCREENING COMPOUNDS AND COMPOSITIONS

BACKGROUND OF THE INVENTION

It is known that sunlight accelerates the aging of skin and even gives rise to skin cancer, these undesired effects being caused by UV radiation. There are compounds which are acceptable for use in cosmetic light screening compositions that are effective UV-filters with absorption maxima in the UV-A range as well as the UV-B range. However, there are few compounds available that have an absorption maxima between those of the known UV-A and UV-B filters, and those that are known are often not used by formulators because of the properties of those filters.

BRIEF SUMMARY OF THE INVENTION

The present invention relates to a cosmetic light-screening composition, the use of the cosmetic light-screening composition for the protection of the human skin and human hair against the ultraviolet radiation of wavelengths between about 280 and 400 nm and compounds contained in the composition and the use of these compounds as UV filters. Particularly, the compounds of the present invention have absorption maxima that fall between the maxima for UV-A and UV-B.

It has now been found that the compounds of the formula I

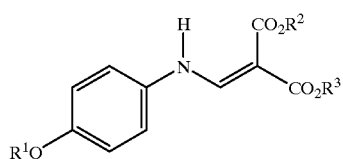

I wherein $R^1$ represents a $C_{1-8}$ straight or branched alkyl chain, and $R^2$ and $R^3$ each independently represent a $C_{1-8}$ straight or branched alkyl chain are exellent UV filters concerning skin compatibility and stability (light, heat, moisture); they make a strong contribution to the UV protection of the skin and therewith cause a delay in skin ageing. In particular these UV filters also have an outstanding photostability.

It has also been found that the compounds of formula I have their absorption maxima between those of UV A-filters like e.g. 4-tert-butyl-4'-methoxydibenzoylmethane and those of UV B filters and especially and surprisingly increase the protective effect of UV B filters, i.e. of substances which mainly absorb the erythema-producing UV-B radiation in the region of about 290 to about 320 nm, although the absorption maximum of the compound of formula I does not lie in this region, but in the region of about 320 to 340 nm, i.e. between the maxima of UVA and UVB radiation.

The only types of UV-filters available for cosmetic use which also absorb in these regions are the benzophenones and menthyl anthranilate. Many formulators don't use them for various reasons, e.g. very low extinction compared to the compounds of formula I.

Alkoxyanilinomethylene-propanedioic acid esters of the formula I are known from U.S. Pat. No. 3,079,366 and from W. O. Kermack, N. E. Storey, J. Chem. Soc 607 (1950); T. Takahashi, S. Senda, J. Pharm. Soc. Jpn., 71, 1112 (1952).

Specifically disclosed are methoxy-ethoxy- and butoxy-anilinomethylene-propanedioic ethyl esters. But nothing is disclosed about the use of these compounds for cosmetic purposes, especially to use these compounds in skin care or hair care.

An UV-filter should show a large solubility in cosmetic solvant in order to be formulated in a reasonable concentration. For instance, a 6% UV-filter content in a classical o/w emulsion having a 70% water content requires a solubility up to 20% in the oil phase. Surprisingly, it has been found that the compounds of formula I show solubility up to 20% in many cosmetic solvents like caprylic capric triglyceride, propylene glycol dicaprylate/dicaprate, $C_{12-15}$ alkyl benzoate, propylene glycol monoisostearate, diisopropyladipate.

Objects of the present invention are accordingly novel compounds of formula I, light screening preparations for cosmetic purposes containing at least one of the compounds of formula I above, preferably in combination with at least one UV B filter agent and at least one UV A filter agent, and the use of compounds of formula I as light screening agents, especially for cosmetic purposes.

DETAILED DESCRIPTION OF THE INVENTION

According to the present invention there is provided a cosmetic light-screening composition for protecting human skin or human hair against ultraviolet radiation containing in a cosmetically acceptable carrier at least one compound of formula I

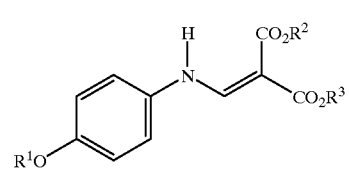

I wherein $R^1$ represents a $C_{1-8}$ straight or branched alkyl chain, $R^2$ and $R^3$ each independently represent a $C_{1-8}$ straight or branched alkyl chain.

The term "$C_{1-8}$ straight or branched alkyl chain" refers to groups like methyl, ethyl, n-propyl, isopropyl, n-butyl, tert.butyl, pentyl, heptyl, 2-ethylhexyl and the like.

Preferred are compounds wherein $R^2$ and $R^3$ each independently represent methyl, ethyl, pentyl or 2-ethylhexyl.

The group $R^1$ is preferably methyl, ethyl or n-butyl.

Thus, the following compounds are preferred:

compounds wherein $R^1$, $R^2$ and $R^3$ are methyl (Ex.1) or ethyl (Ex.4); or $R^1$ is ethyl and $R^2$ and $R^3$ are methyl (Ex.2) or 2-ethylhexyl (Ex.6); or $R^1$ is n-butyl and $R^2$ and $R^3$ are methyl. (Ex.3) or ethyl (Ex.5).

Most preferred is a compound according to Example 4 wherein $R^1$, $R^2$ and $R^3$ are ethyl.

The cosmetic light screening composition comprises preferably 0.1 to 10% by weight, more preferably 0.5 to 5% by weight, of the compound(s) of formula I, in particular 1 to 3% by weight of the compound(s) of formula I.

The cosmetic light screening composition may in addition comprise at least one UV-B filter agent with an absorption maximum at about 300 to 320 nm and at least one UV-A filter agent with an absorption maximum at ≧340 nm, especially at between 340 and 360 nm, particularly one UV-A filter agent having an absorption maximum at 356 nm. Specifically this UV-A filter agent is 4-tert-butyl-4'-methoxydibenzoylmethane. Generally the UV-A filter agent can be choosen out of the group consisting of 2-methyldibenzoylmethane, 4-methyl-dibenzoyl-methane, 4-tert-butyldibenzoylmethane, 2,4-dimethyldibenzoylmethane, 2,5-dimethyldibenzoylmethane, 4,4'-diisopropyldibenzoylmethane, 4-tert-butyl-4'-methoxydibenzoylmethane, 2-methyl-5-isopropyl-4'-methoxydibenzoylmethane, 2-methyl-5-tert-butyl-4'-methoxydibenzoylmethane, 2,4-dimethyl-4'-methoxydibenzoylmethane and 2,6-dimethyl-4-tert-butyl-4'-methodydibenzoylmethane and terephtalylidene dicamphor sulfonic acid.

The UV-B filter agent is at least one of the group consisting of cinnamates, salicylates, benzophenones, diphenylacrylates triazines, camphor derivates, polymeric UV absorbers specially those described in U.S. Pat. No. 5,403,944 and microfine pigments. Specifically the UV-B filter agent is at least one of the group consisting of pigment metallic oxides of cerium, iron, titanium, zinc or zirconium, especially of titanium or zinc, and polymers with hydrocarbon structure or siloxane structure carrying at least one ultraviolet-light-absorbing group.

The cosmetic light-screening compositions or the compounds of formula I are useful for protecting human skin or human hair against ultraviolet radiation.

The following compounds of formula I are new:

2-(4-Heptoxy-anilinomethylene)-propanedioic acid diethyl ester, 2-(4-Methoxy-anilinomethylene)-propanedioic acid dimethyl ester, 2-(4-Ethoxy-anilinomethylene)-propanedioic acid dimethyl ester, 2-(4-Propoxy-anilinomethylene)-propanedioic acid dimethyl ester, 2-(4-Butoxy-anilinomethylene)-propanedioic acid dimethyl ester, 2-(4-Pentoxy-anilinomethylene)-propanedioic acid dimethyl ester, 2-(4-Hexoxy-anilinomethylene)-propanedioic acid dimethyl ester, 2-(4-Ethoxy-anilinomethylene)-propanedioic acid dipentyl ester, 2-(4-Ethoxy-anilinomethylene)-propanedioic acid ethyl ester pentyl ester, 2-(4-Ethoxy-anilinomethylene)-propanedioic acid di-2-ethyl-hexyl ester and 2-(4-Ethoxy-anilinomethylene)-propanedioic acid ethyl ester 2-ethyl-hexyl ester.

Each of those can be used as an UV filter, especially for cosmetic purposes as said already before. In this respect the following ones are of specific interest:

2-(4-Ethoxy-anilinomethylene)-propanedioic acid dipentyl ester, 2-(4-Ethoxy-anilinomethylene)-propanedioic acid ethyl ester pentyl ester, 2-(4-Ethoxy-anilinomethylene)-propanedioic acid di-2-ethyl-hexyl ester and 2-(4-Ethoxy-anilinomethylene)-propanedioic acid ethyl ester 2-ethyl-hexyl ester.

The compounds represented by formula I (known and new compounds) are conveniently prepared by conventional methods as disclosed in U.S. Pat. No. 3,079,366 which is incorporated by reference herein and which may be described briefly as follows:

Reaction of an aniline derivatives ($C_1$–$C_8$ alkoxyaniline) with the appropriately substituted alkoxyalkylene-malono derivative with or without a solvent.

As cosmetically acceptable carrier usual for light screening agents in the scope of the present invention there can be used any conventional preparation which corresponds to the cosmetic requirements, e.g. creams, lotions, emulsions, salves, gels, solutions, sprays, sticks and milks; see e.g. Kosmetik, Entwicklung, Herstellung and Anwendung Kosmetischer Mittel, ed. Wilfried Umbach, Georg Thieme Vertrag Stuttgart—New York 1988; Sunscreens, Development, Evulation and Regulatory Aspects, ed. N.Y. Lowe, N. A. Shaat, Marcel Decker, Inc. New York Basel, 1990.

Having regard to their lipophility, the compounds of formula I can be incorporated well in oil-containing and fat-containing cosmetic preparations.

With respect to the lipophility, the novel compounds fulfil the criteraia which are required in the present instance, namely a solubility in cosmetic solvents, such as e.g.Miglyol 812N (caprylic capric triglyceride), Miglyol 840 (propylene glycol dicaprylate dicaprate), Finsolv TN ($C_{12-15}$ alkyl benzoate), Prisorine 2034 (propylene glycol monoisostearate) or Crodamol DA (diisopropyladipate).

The compound of Example 4 is especially preferred particularly in the just mentioned respect.

Suitable the cosmetic screening formulations takes the form of an oil, a lotion, a gel, a solid stick, an emulsion, e.g. cream, milk or of a vesicular dispersion of ionic or nonionic amphliphilic lipids, an aerosol, a spray, a foam, a powder, a shampoo, a hair conditioner or lacquer or a make-up or the like.

In case a cosmetic formulation for the protection of human hair is prepared by at least one compound of formula I the suitable formulations are shampoos, conditioners, lotions, gels, emulsions, dispersions, lacquers or the like. The preparation of all these formulations is well known to the skilled artisan.

The usual solvents known to the skilled artisan can be used for the preparation of these forms, e.g. oils, waxes, alcohols, polyols. The preferred agents are fatty acids, esters, fatty alcohols, but also ethanol, isopropanol, propylene glycol, glycerine or the like are useful.

The cosmetic formulations may contain further adjuvants, e.g. further solvents, thickeners, emollients, emulsifiers, humectants, tensides, preservatives, antifoams, fragrances, oils, waxes, lower polyols and monohydric alcohols, propellants, silicones, colourings and pigments or the like.

An important advantage of the novel light-screening composition or the compounds of formula I stems from the fact that the artisan skilled in the art is completely free in the choice regarding the material used for the filtration of the UV-B and UV-A radiation as already said above. But for UV-A filtration the most preferred UV-A filter agent is 4-tert-butyl-4'-methoxydibenzoylmethane, this is especially used in combination with 2-(4-ethoxy-anilinomethylene)-propanedioic acid diethyl ester.

Further advantages, characteristics and details are disclosed by the following examples.

EXAMPLE 1

2-(4-Methoxy-anilinomethylene)-propanedioic acid dimethyl ester

To a solution of 12.3 g (0.1 Mol) of p-Anisidine in 50 ml of ethanol, a solution of 17.4 g (0.1 Mol) of Dimethyl methoxymethylenemalonate in 70 ml of ethanol was added dropwise with stirring at room temperature. After an additional hour of stirring at that temperature, the reaction mixture was cooled with an ice bath and the product cristallised spontanously. The crude solid material was isolated by filtration and washed with ethanol and gave 12.9 g of the title product which is a white solid melting at 89–91° C., UV 328 nm (E=899).

EXAMPLE 2

2-(4-Ethoxy-anilinomethylene)-propanedioic acid dimethyl ester

Same preparation as in example 1 where one equivalent of p-Phenetidine was used instead of p-Anisidine.

19.8 g of the title compound was obtained which is a white solid melting at 66–67° C., UV 328 nm (E=879).

EXAMPLE 3

2-(4-Butoxy-anilinomethylene)-propanedioic acid dimethyl ester a) Preparation of 2-(4-Hydroxy-anilinomethylene)-propanedioic acid dimethyl ester.

To a solution of 16.4 g (0.15 Mol) of 4-Aminophenol in 100 ml of ethanol, a solution of 26.1 g (0.15 Mol) of Dimethyl methoxymethylenemalonate in 70 ml of ethanol was added dropwise at room temperature. After an additional 10 minutes of stirring at that temperature the crude solid material was isolated by filtration and washed with ethanol and gave 34.3 g of a white solid which was then used without further purification.

b) To a mixture of 7 g (28 mMol) of 2-(4-Hydroxy-anilinomethylene)-propanedioic acid dimethyl ester, 3.9 g (28 mMol) of Potassium carbonate in 50 ml of dimethylformamide, 7.3 g (28 mMol) of Butyl iodide were added dropwise with stirring at room temperature. The reaction mixture was heated at 80° C. for 24 hours. Then the reaction mixture was poured into 50 ml of water and extracted three times with ethyl acetate. The organic layer was washed with a solution of sodium hydroxyde (15%) and thereafter with water, dried and evaporated and gave 4.5 g of the title compound which is a white solid melting at 46–47° C., UV 328 nm (E=685).

EXAMPLE 4

2-(4-Ethoxy-anilinomethylene)-propanedioic acid diethyl ester

The preparation was the same as in example 1. But one equivalent of p-Phenetidine was used instead of p-Anisidine and one equivalent of diethyl ethoxymethylenemalonate was used instead of dimethyl methoxymethylenemalonate. Ethanol was replaced by hexane. 21 g of the title compound was obtained which is a white solid melting at 55–56° C., UV 329 nm (E=802).

EXAMPLE 5

2-(4-Butoxy-anilinomethylene)-propanedioic acid diethyl ester

The preparation was the same as in example 3. But one equivalent of diethyl ethoxymethylenemalonate was used instead of dimethyl methoxy-methylenemalonate. 3.1 g of the title compound was obtained which is a white solid melting at 54–55° C., UV 329 nm (E=714).

EXAMPLE 6

2-(4-Ethoxy-anilinomethylene)-propanedioic acid di-2-ethyl-hexyl ester and 2-(4-Ethoxy-anilinomethylene)-propanedioic acid ethyl ester 2-ethyl-hexyl ester A mixture of 18.4 g (60 mMol) of 2-(4-Ethoxy-anilinomethylene)-propanedioic acid diethyl ester, 430 mg of titanium(IV) isopropoxide in 70 ml of 2-Ethyl-hexanol was stirred at 150° C. for 4 hours. The reaction mixture was concentrated under reduced pressure (80° C., 6 mbar) to get a yellow oil. This oil was dissolved into 100 ml of ethyl acetate and 5 ml of water, stirred for 10 min and dried over anhydrous magnesium sulfate. The flaky suspension was filtered and concentrated under reduced pressure and gave 26.8 g of an yellow oil. The two title products were isolated by flash chromatography using hexane:ethyl acetate 10:1 as eluant.

23.6 g of 2-(4-Ethoxy-anilinomethylene)-propanedioic acid di-2-ethyl-hexyl ester was obtained which is a yellow oil, UV 329 nm (E=567).

1.8 g of Ethoxy-anilinomethylene)-propanedioic acid ethyl ester and 2-ethyl-hexyl ester which is a yellow oil UV 329 nm (E=632).

EXAMPLE 7

2-(4-Ethoxy-anilinomethylene)-propanedioic acid dipentyl ester and 2-(4-Ethoxy-anilinomethylene)-propanedioic acid ethyl ester pentyl ester The preparations were the same as in example 6 where n-pentanol was used instead of 2-Ethyl-hexanol. The two title products were isolated by flash chromatography using hexane:ethyl acetate 8:1 as eluant.

16.6 g of 2-(4-Ethoxy-anilinomethylene)-propanedioic acid dipentyl ester was obtained which is a yellow oil, UV 329 nm (E=651).

2.5 g of Ethoxy-anilinomethylene)-propanedioic acid ethyl ester pentyl ester was obtained which is a yellow oil UV 329 nm (E=725).

EXAMPLE 8

Preparation of formula type: water in oil emulsion

| Ingredients | % w/w |
|---|---|
| A) | |
| Product from example 6 (di-2-ethyl-hexyl ester) | 6 |
| Butyl Methoxydibenzoylmethane (Parsol 1789) | 1.5 |
| Octyl methoxycinnamate (Parsol MCX) | 3 |
| Polyglyceryl-3 Diisostearate | 5 |
| Glyceryl oleate | 3 |
| Cetearyl alcohol | 2 |
| Mineral oil | 10 |
| Coco caprylate/caprate | 10 |
| Titanium Dioxyde coated with Dimethicone | 2 |
| Octyldodecanol | 2 |
| Butylhydroxytoluene | 0.1 |
| Phenoxyethanol and Methylparaben and Ethylparaben and Propylparaben and Butylparaben | 0.6 |

-continued

| Ingredients | % w/w |
| --- | --- |
| B) | |
| Glycerol (86%) | 5 |
| Phenylbenzimidazole Sulfonic Acid (Parsol HS) | 2 |
| Disodium EDTA | 0.1 |
| Water | 47.7 |

Part A and part B were mixed separately at 85° C. and then combined under stirring. Finally, the pH was corrected to 7 with potassium hydroxide 10% or citric acid 10% if necessary.

EXAMPLE 9

Preparation of formula type: water in oil emulsion (soft cream)

| Ingredients | % w/w |
| --- | --- |
| A) | |
| Product from example 4 | 5 |
| POP-POE Glycerol sorbitan fatty acids Esters | 5 |
| Heptamethylnonane | 5 |
| Paraffin | 9 |
| PPG-(15)-stearyl alcohol and cyclomethicone | 2 |
| silica | 0.4 |
| Butylhydroxytoluene | 0.1 |
| Phenoxyethanol and Methylparaben and Ethylparaben and Propylparaben and Butylparaben | 0.6 |
| B) | |
| Sodium chloride | 0.5 |
| POE-30 Sorbitol | 1.5 |
| Glycerol (86%) | 2.5 |
| Disodium EDTA | 0.1 |
| Water | 68.3 |

Part A and part B were mixed separately at 85° C. and then combined under stirring. Finally, the pH was corrected to 7 with potassium hydroxide 10% or citric acid 10% if necessary.

EXAMPLE 10

Formula type: silicon in water emulsion (lotion)

| Ingredients | % w/w |
| --- | --- |
| A) | |
| Product from example 5 | 2 |
| Cyclomethicone pentamere and Aluminium magnesium hydroxy stearate | 9 |
| Cyclomethicone and Dimethicone Copolyol | 10 |
| Cyclomethicone | 5 |
| PPG-3 Myristyl ether | 2 |
| Titanium dioxyde coated with Dimethicone | 2 |
| C12–15 Alkylbenzoate | 10 |
| Butylhydroxytoluene | 0.1 |
| Phenoxyethanol and Methylparaben and Ethylparaben and Propylparaben and Butylparaben | 0.6 |

-continued

| Ingredients | % w/w |
| --- | --- |
| B) | |
| Sodium chloride | 0.5 |
| Tocopherylacetate | 2 |
| Disodium EDTA | 0.1 |
| Water | 56.7 |

Part A and part B were mixed separately at 85° C. and then combined under stirring. Finally, the pH was corrected to 7 with potassium hydroxide 10% or citric acid 10% if necessary.

EXAMPLE 11

Preparation of formula type: oil in water emulsion

| Ingredients | % w/w |
| --- | --- |
| A) | |
| Product from example 4 | 4 |
| Octyl methoxycinnamate (Parsol MCX) | 3 |
| Butyl methoxydibenzoylmethane (Parsol 1789) | 1.5 |
| 4-Methylbenzilidene Camphor (Parsol 5000) | 3 |
| Glyceryl Monomyristate | 4 |
| Cetyl alcohol | 1 |
| Coco caprilate caprate | 15 |
| Isopropyl myristate | 5 |
| PVP-Eicosen copolymer | 2 |
| Butylhydroxytoluene | 0.1 |
| Disodium EDTA | 0.1 |
| Phenoxyethanol and Methylparaben and Ethylparaben and Propylparaben and Butylparaben | 0.6 |
| B) | |
| POE-POP Block copolymer | 2 |
| Water | 38.7 |
| Carbomer 981 | 10 |
| Propylene glycol | 10 |

Part A and part B were mixed separately at 85° C. and then combined under stirring. Finally, the pH was corrected to 7 with potassium hydroxide 10% or citric acid 10% if necessary.

EXAMPLE 12

Formula type: oil in water emulsion

| Ingredients | % w/w |
| --- | --- |
| A) | |
| Product from example 4 | 3.5 |
| Octyl methoxycinnamate (Parsol MCX) | 3 |
| Butyl methoxydibenzoylmethane (Parsol 1789) | 1.5 |
| 4-Methylbenzilidene camphor (Parsol 5000) | 3 |
| Glyceryl monomyristate | 4 |
| Cetyl alcohol | 1 |
| Coco caprilate caprate | 5 |
| Caprilic capric triglyceride | 5 |
| PVP-Eicosen copolymer | 1 |
| Butylhydroxytoluene | 0.1 |
| Disodium EDTA | 0.1 |
| Phenoxyethanol and Methylparaben and Ethylparaben and Propylparaben and Butylparaben | 0.6 |

-continued

| Ingredients | % w/w |
| --- | --- |
| B) | |
| Sorbitan ester and Sucrose ester | 4 |
| Water | 48.2 |
| Carbomer 981 | 10 |
| Propylene glycol | 10 |

Part A and part B were mixed separately at 85° C. and then combined under stirring. Finally, the pH was corrected to 7 with potassium hydroxide 10% or citric acid 10% if necessary.

The emulsions of Examples 8, 11 and 12 showed a broad filter activity over the complete UV region of about 280 to 400 nm with a broad plateau maximum in the range of about 300 to 360 nm.

We claim:

1. A cosmetic light-screening composition for protecting human skin or human hair against ultraviolet radiation containing in a cosmetically acceptable carrier at least one compound of formula I

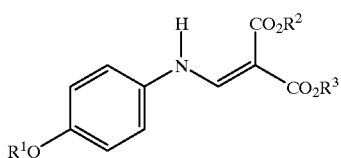

wherein $R^1$ represents a $C_{1-8}$ straight or branched alkyl chain, and $R^2$ and $R^3$ each independently represent a $C_{1-8}$ straight or branched alkyl chain.

2. A cosmetic light-screening composition according to claim 1 wherein $R^1$ represents methyl, ethyl or n-butyl, and $R^2$ and $R^3$ each independently represents methyl, ethyl, pentyl, 2-ethyl-hexyl.

3. A cosmetic light-screening composition according to claim 2 wherein $R^1$, $R^2$ and $R^3$ are ethyl.

4. A cosmetic light-screening composition according to claim 1 comprising from about 0.1 to about 10% by weight of at least one of the compounds of formula I.

5. A cosmetic light-screening composition according claim 2 comprising from about 0.5 to about 5% by weight of at least one of the compounds of formula I.

6. A cosmetic light-screening composition according to claim 2 comprising from about 1 to about 3% by weight of at least one of the compounds of formula I.

7. A cosmetic light-screening composition according to claim 3 comprising from about 1 to about 3% by weight of at least one of the compounds of formula I.

8. A cosmetic light-screening composition according to claim 1 further comprising at least one UV-B filter agent with an absorption maximum between about 300 to about 320 nm and at least one UV-A filter agent with an absorption maximum between about 340 and about 360 nm.

9. A cosmetic light-screening composition according to claim 5 further comprising at least one UV-B filter agent with an absorption maximum between about 300 to about 320 nm and at least one UV-A filter agent with an absorption maximum between about 340 and about 360 nm.

10. A cosmetic light-screening composition according to claim 6 further comprising at least one UV-B filter agent with an absorption maximum between about 300 to about 320 nm and at least one UV-A filter agent with an absorption maximum between about 340 and about 360 nm.

11. A cosmetic light-screening composition according to claim 7 further comprising at least one UV-B filter agent with an absorption maximum between about 300 to about 320 nm and at least one UV-A filter agent with an absorption maximum between about 340 and about 360 nm.

12. A cosmetic light-screening composition according to claim 9 wherein the at least one UV-A filter agent is selected from the group consisting of 2-methyldibenzoylmethane, 4-methyl-dibenzoyl-methane, 4-tert-butyldibenzoyl-methane, 2,4-dimethyldibenzoylmethane, 2,5-dimethyldibenzoylmethane, 4,4'-diisopropyldibenzoylmethane, 4-tert-butyl-4'-methoxydibenzoylmethane, 2-methyl-5-isopropyl-4'-methoxydibenzoylmethane, 2-methyl-5-tert-butyl-4'-methoxydibenzoylmethane, 2,4-dimethyl-4'-methoxydibenzoylmethane, 2,6-dimethyl-4-tert-butyl-4'-methoxydibenzoylmethane and terephthalylidene dicamphor sulfonic acid.

13. A cosmetic light-screening composition according to claim 11 wherein the at least one UV-A filter agent is selected from the group consisting of 2-methyldibenzoylmethane, 4-methyl-dibenzoyl-methane, 4-tert-butyldibenzoyl-methane, 2,4-dimethyldibenzoylmethane, 2,5-dimethyldibenzoylmethane, 4,4'-diisopropyldibenzoylmethane, 4-tert-butyl-4'-methoxydibenzoylmethane, 2-methyl-5-isopropyl-4'-methoxydibenzoylmethane, 2-methyl-5-tert-butyl-4'-methoxydibenzoylmethane, 2,4-dimethyl-4'-methoxydibenzoylmethane, 2,6-dimethyl-4-tert-butyl-4'-methoxydibenzoylmethane and terephtalylidene dicamphor sulfonic acid.

14. A cosmetic light-screening composition according to claim 12 wherein the UV-A filter agent is 4-tert-butyl-4'-methoxydibenzoylmethane.

15. A cosmetic light-screening composition according to claim 13 wherein the UV-A filter agent is 4-tert-butyl-4'-methoxydibenzoylmethane.

16. A cosmetic light-screening composition according to claim 8 wherein the at least one UV-B filter agent is selected from the group consisting of cinnamates, salicylates, benzophenones, diphenylacrylates triazines, camphor derivates, polymeric UV-absorbers or pigment metallic oxides of cerium, iron, titanium, zinc or zirconium, especially of titanium or zinc, and polymers with hydrocarbon structure or siloxane structure carrying at least one ultraviolet-light-absorbing group.

17. A cosmetic light-screening composition according to claim 12 wherein the at least one UV-B filter agent is selected from the group consisting of cinnamates, salicylates, benzophenones, diphenylacrylates triazines, camphor derivates, polymeric UV-absorbers or pigment metallic oxides of cerium, iron, titanium, zinc or zirconium, especially of titanium or zinc, and polymers with hydrocarbon structure or siloxane structure carrying at least one ultraviolet-light-absorbing group.

18. A cosmetic light-screening composition according to claim 13 wherein the at least one UV-B filter agent is selected from the group consisting of cinnamates, salicylates, benzophenones, diphenylacrylates triazines, camphor derivates, polymeric UV-absorbers or pigment metallic oxides of cerium, iron, titanium, zinc or zirconium, especially of titanium or zinc, and polymers with hydrocarbon structure or siloxane structure carrying at least one ultraviolet-light-absorbing group.

19. A cosmetic light-screening composition according to claim 14 wherein the at least one UV-B filter agent is selected from the group consisting of cinnamates, salicylates, benzophenones, diphenylacrylates triazines, camphor derivates, polymeric UV-absorbers or pigment metallic oxides of cerium, iron, titanium, zinc or zirconium, especially of titanium or zinc, and polymers with hydrocarbon structure or siloxane structure carrying at least one ultraviolet-light-absorbing group.

20. A cosmetic light-screening composition according to claim 15 wherein the at least one UV-B filter agent is selected from the group consisting of cinnamates, salicylates, benzophenones, diphenylacrylates triazines, camphor derivates, polymeric UV-absorbers or pigment metallic oxides of cerium, iron, titanium, zinc or zirconium, especially of titanium or zinc, and polymers with hydrocarbon structure or siloxane structure carrying at least one ultraviolet-light-absorbing group.

21. The cosmetic light screening composition of claim 1 wherein the at least one compound of formula I is selected from the group consisting of 2-(4-Heptoxy-anilinomethylene)-propanedioic acid diethyl ester, 2-(4-Methoxy-anilinomethylene)-propanedioic acid dimethyl ester, 2-(4-Ethoxy-anilinomethylene)-propanedioic acid dimethyl ester, 2-(4-Propoxy-anilinomethylene)-propanedioic acid dimethyl ester, 2-(4-Butoxy-anilinomethylene)-propanedioic acid dimethyl ester, 2-(4-Pentoxy-anilinomethylene)-propanedioic acid dimethyl ester, 2-(4-Hexoxy-anilinomethylene)-propanedioic acid dimethyl ester, 2-(4-Ethoxy-anilinomethylene)-propanedioic acid dipentyl ester, 2-(4-Ethoxy-anilinomethylene)-propanedioic acid ethyl ester pentyl ester, 2-(4-Ethoxy-anilinomethylene)-propanedioic acid di-2-ethyl-hexyl ester and 2-(4-Ethoxy-anilinomethylene)-propanedioic acid ethyl ester 2-ethyl-hexyl ester.

22. The cosmetic light screening composition of claim 1 wherein the at least one compound of formula I is 2-(4-Ethoxy-anilinomethylene)-propanedioic acid dipentyl ester.

23. The cosmetic light screening composition of claim 1 wherein the at least one compound of formula I is 2-(4-Ethoxy-anilinomethylene)-propanedioic acid ethyl ester pentyl ester.

24. The cosmetic light screening composition of claim 1 wherein the at least one compound of formula I is 2-(4-Ethoxy-anilinomethylene)-propanedioic acid di-2-ethyl-hexyl ester.

25. The cosmetic light screening composition of claim 1 wherein the at least one compound of formula I is 2-(4-Ethoxy-anilinomethylene)-propanedioic acid ethyl ester 2-ethyl-hexyl ester.

26. A method for protecting human skin or human hair against ultraviolet radiation comprising administering an effective amount of a cosmetic light screening composition of claim 1.

27. A method for protecting human skin or human hair against ultraviolet radiation comprising administering an effective amount of a cosmetic light screening composition of claim 20.

* * * * *